United States Patent [19]

Wogoman

[11] Patent Number: 5,030,310
[45] Date of Patent: Jul. 9, 1991

[54] ELECTRODE FOR ELECTROCHEMICAL SENSORS

[75] Inventor: Frank W. Wogoman, South Bend, Ind.

[73] Assignee: Miles Inc., Elkhart, Ind.

[21] Appl. No.: 467,363

[22] Filed: Jan. 19, 1990

Related U.S. Application Data

[62] Division of Ser. No. 749,817, Jun. 28, 1985, Pat. No. 4,938,860.

[51] Int. Cl.$^5$ .............................................. B32B 31/14
[52] U.S. Cl. ..................... 156/252; 204/403; 204/412; 204/415; 204/416; 204/418; 435/817
[58] Field of Search ............... 156/252; 204/403, 412, 204/415, 416, 418; 435/817

[56] References Cited

U.S. PATENT DOCUMENTS

| | | |
|---|---|---|
| 3,260,656 | 7/1966 | Ross ..................... 204/415 |
| 3,926,766 | 12/1975 | Niedrach et al. ..................... 204/415 |
| 3,957,613 | 5/1976 | Macur ..................... 204/415 |
| 4,062,750 | 12/1977 | Butler ..................... 204/403 |
| 4,161,437 | 7/1979 | Fleckonstein ..................... 204/415 |
| 4,225,410 | 9/1980 | Pace ..................... 204/412 |
| 4,236,987 | 12/1980 | Schindler et al. ..................... 204/418 |
| 4,454,007 | 6/1984 | Pace ..................... 204/403 |
| 4,490,216 | 12/1984 | McConnell ..................... 204/1 T |
| 4,536,274 | 8/1985 | Papadakis et al. ..................... 204/415 |

*Primary Examiner*—Caleb Weston
*Attorney, Agent, or Firm*—Roger N. Coe

[57] ABSTRACT

A disposable, inexpensive electrode for an electrochemical sensor includes a laminated anode and a laminated cathode. The anode is a film substrate with anodic material such as platinum deposited on the substrate. The cathode is also a film substrate with cathodic material such as silver deposited on the substrate. The anode and cathode can be laminated with an intermediate layer of dielectric material. A working surface is provided on the electrode and defined, in part, by the anode and cathode. One procedure for defining the working surface is to fabricate spaced openings in the cathode film and the layer of dielectric material. The openings in the cathode film and dielectrical layer are aligned and the exposed surfaces of the anode and cathode define the working area. An enzyme, such as glucose oxidase, is bonded to the exposed anode and a membrane is applied over the working area and enzyme. The membrane is preferably a silicone water-based elastomer. The laminated anode, cathode and dielectric layer are then severed to form individual electrodes each including a working area.

5 Claims, 1 Drawing Sheet

ELECTRODE FOR ELECTROCHEMICAL SENSORS

This is a division of U.S. application Ser. No. 749,817, filed June 28, 1985, now U.S. Pat. No. 4,938,860.

BACKGROUND OF THE INVENTION

1. Field of the Invention

The present invention relates to a new and improved electrode for electrochemical sensors and to a new and improved method of fabricating electrodes for electrochemical sensors; and more specifically, to a new and improved disposable, inexpensive electrode for electrochemical sensors and a method of fabricating the electrode.

2. Description of the Prior Art

Products that measure fluctuations in a person's blood sugar, or glucose levels have become everyday necessities for many of the nation's seven million diabetics. Because this disorder can cause dangerous anomalies in blood chemistry and is believed to be a contributor to vision loss and kidney failure, most diabetics need to test themselves periodically and adjust their glucose count accordingly, usually with insulin injections. Patients who are insulin dependent—about 10% to 15% of diabetics—are instructed by doctors to check their blood-sugar levels as often as four times daily.

For years the solution for diabetics was one of several urinanalysis kits that, despite repeated improvements, provided imprecise measurements of glucose in the blood. The first such kits used tablets. This early testing procedure is described in U.S. Pat. Nos. 2,387,244 and 3,164,534. Later, reagent strips for urine testing were developed. Testing using urine, however, is limited in accuracy. The renal threshhold for glucose spillage is different for each individual. Moreover, sugar in urine is a sign that the sugar level is too high and has been too high for several hours. This is due to the delay in sugar reaching the urine.

More accurate readings are possible by taking readings from blood. The advent of home blood tests is considered by some to be the most significant advance in the care of diabetics since the discovery of insulin in 1921. Home blood glucose testing was made available with the development of reagent strips for whole blood testing. Reagent strips of this type are described in U.S. Pat. Nos. 3,164,534 and 3,092,465. A breakthrough in self-care came in 1979, when the Ames division of Miles Laboratories brought out its Visidex home blood test. Visidex consists of chemically coated plastic strips. When blood drawn by pricking a finger is placed on one of these disposable strips, the resulting color change can be compared with a color-coded glucose scale included in the kits or a reflectometer can be used.

The advantage of the current technology available for home use, the reagent strip, is low cost (roughly fifty cents per use) and a one minute response time. There are significant problems with reagent strips, however. Test timing using reagent strips is very critical. Exactly sixty seconds must elapse from the time a blood sample is placed on a strip to when it is removed by rinsing. The color on the strip must then be compared with a chart. This time constraint and the necessity to ascertain differences in shades of colors results in the technique being very user sensitive.

An alternative to reagent strips is a glucose sensor using an electrode. Electrodes are more costly and the technology is more complicated but the life of an electrode is weeks or months as compared to the single use of a reagent strip. The response time of electrodes is quick and electrodes are not user sensitive resulting in increased accuracy over reagent strips.

Electrodes in electrochemical glucose sensors utilize an enzyme to convert glucose to an electroactive product which is then analyzed electrochemically. The reactions for this electrode are given in the following equations:

$$C_6H_{12}O_6 + O_2 + H_2O = C_6H_{12}O_7 + H_2O_2$$

$$H_2O_2 = O_2 + 2H^+ + 2e^-$$

$$O_2 + 4H^+ = 2H_2O$$

In the first equation glucose is oxidized by oxygen to form gluconolactone and hydrogen peroxide. This reaction is catalyzed by the enzyme glucose oxidase. The hydrogen peroxide may be detected either by oxidation as shown in the second equation or by measuring the decrease in oxygen partial pressure by the reaction shown in the third equation. In either case a current is obtained which is related to the glucose concentration. The oxidation of the hydrogen peroxide is done at a platinum electrode and the reduction may be done at either a platinum or a silver electrode.

In these electrodes, diffusion of glucose through membranes and reactions of glucose in membranes is of concern. In known electrodes, glucose and oxygen from diluted blood as well as many interferents diffuse through a primary membrane. As glucose diffusing through this membrane reaches a second membrane, glucose oxidase catalyzes the conversion of the glucose to hydrogen peroxide and gluconolactone. The hydrogen peroxide may diffuse back through the primary membrane or it may further diffuse through the second membrane where it can be oxidized to the electrode and produce a current used for analysis. The secondary membrane prevents passage to the electrode of substantially everything except the hydrogen peroxide.

Glucose electrochemical sensors are essentially made up of two major components; a permanent or factory replaceable electrode and a user replaceable, disposable membrane assembly including a primary membrane and a secondary membrane. The electrode is based on a Clark electrode operating in the hydrogen peroxide mode. An electrode of this type is described in U.S. Pat. No. 2,913,386. The Clark electrode includes a platinum anode and a silver cathode. A voltage of 0.7 volts is applied to the electrode and current between the cathode and anode is measured.

The primary membrane is used to separate high molecular and cellular components of the blood from the glucose. This membrane must be permeable to glucose but relatively impermeable to the larger molecular and cellular components of blood. The typical primary membrane is not whole blood compatible, since to do so requires a surface treatment. Due its this incompatibility, the primary membrane is quickly fouled by protein deposits or blood clots requiring the membrane assembly to be replaced by the user.

Before electrochemical sensors can be made for use in the home, technology must be advanced to allow measurements using whole blood. This has not been achievable in electrochemical sensors to date because primary membranes presently used are not whole blood compatible and are quickly fouled by contaminants in whole blood. Many of the disadvantages of prior sensors could be eliminated if a longer lasting membrane could be provided. A membrane of this type is disclosed in co-pending application Serial No. 749,724 filed concurrently with the present application and assigned to the assignee of the present invention. A membrane of this type, however, is bonded to the electrode. When the membrane fails, the membrane and electrode must be replaced rather than only the membrane, and it is desirable to provide an inexpensive electrode that can be disposed of after several uses.

SUMMARY OF THE INVENTION

An object of the present invention is to provide a new and improved electrode for an electrochemical sensor.

Another object of the present invention is to provide a disposable electrode for a glucose sensor.

A further object of the present invention is to provide a new and improved electrode for a glucose sensor that has a life of several weeks and is cost competitive with present glucose testing devices.

A still further object of the present invention is to provide a new and improved method of fabricating a disposable electrode for glucose sensors.

Another object of the present invention is to provide a new and improved laminated electrode for a glucose sensor.

Briefly, the present invention is directed to a new and improved electrode for an electrochemical sensor and to a new and improved method for fabricating the electrode. The electrode is inexpensive and easily replaced by a user of the sensor. The electrode is the result of the discovery that only a few molecular layers of the anode and cathode material of an electrode are actually required for the electrode to function. With this discovery it was determined lamination technology could be utilized. Using lamination technology, platinum or other anodic material is vapor deposited or sputtered onto a thin film to define the anode of the electrode. Similarly, the cathode is defined by depositing silver or similar cathodic material onto a film.

One electrode fabrication procedure involves laminating the cathode film onto the anode film with a layer of dielectric material between the two films. An opening is fabricated in the cathode and the dielectric layer, thus defining an anode working area. Apertures or similar access structure are then fabricated in the electrode to allow connection to electrical contacts.

The electrode of the present invention is inexpensive allowing it to be disposable. By being disposable, the sensor described in copending application Serial No. 749,724 filed June 28, 1985, which may use the electrode of the present is feasible for home use since the cost per use is competitive with reagent strips.

The electrode is also easily replaceable by a user of the sensor. This allows a home user to conduct as many tests as needed and easily replace the electrode when it no longer functions. The electrode is constructed so that the home user need not recalibrate the sensor or use a technician to replace the electrode.

BRIEF DESCRIPTION OF THE DRAWINGS

The above and other objects and advantages and novel features of the present invention will become apparent from the following detailed description of the preferred embodiment of the invention illustrated in the accompanying drawings wherein.

DETAILED DESCRIPTION OF THE PREFERRED EMBODIMENTS

Prior art electrochemical sensors used for measuring glucose in whole blood include a disposable membrane assembly and a semipermanent electrode. Typically, the electrode is replaceable by a skilled service person. A new electrochemical chemical sensor for home use is disclosed in application Serial No. 749,724, filed concurrently with this application and assigned to the assignee of the present invention. The new sensor uses a whole blood compatible membrane integrally bonded to the electrode. In the new sensor, the electrode, enzyme layer and membrane are an integral unit increasing the efficiency and response time of the electrode; however, due to the limited life of the membrane, a disposable interface between the instrumental system of the sensor and the membrane is necessary. The disposable portion must be inexpensive in order to maintain the cost per use of the sensor competitive with current home testing devices, such as reagent strips. The disposable portion should also be easily replaceable allowing replacement by a home user.

In prior art sensors, the disposable portion is the membrane assembly. However, because the present electrode utilizes only a few molecular layers of the anode and cathode materials, a relatively inexpensive disposable electrode can be produced using vapor deposition and lamination technologies to provide a laminated electrode that requires little precious material. Such a disposable electrode was made possible by the discovery that only the top few molecular layers of the anode and cathode of an electrode are active.

Referring now to the drawings and particularly to FIGS. 1-5, there is illustrated a laminated electrode 10 constructed in accordance with the principles and method of the present invention. Electrode 10, in one embodiment, includes an anode 12 which can be platinum foil or a film with a layer of platinum vapor deposited or otherwise deposited onto the film. The cathode 14 of electrode 10 is similarly fabricated from silver foil or silver vapor deposited onto a film. In accordance with the discovery of the surface phenomenum that only a few molecular layers of the anode and cathode are used, or are active, the thicknesses of the foils or the deposited metals utilized on the anode and cathode 12 and 14 are only a few molecular layers. It is to be understood that platinum and silver are described as the preferred metals for the anode 12 and cathode 14, respectively, but other materials, well known in the art, can be used. The anode 12 and cathode 14 of electrode 10 are electrically isolated by a layer of dielectric material 16 and the upper surface of cathode 14 can be protected by a top sheet of dielectric material 18.

To allow electrode 10 to function as an enzyme electrode in an electrochemical sensor, a working area 20 for the measurement of glucose is defined. Working area 20 consists of aligned apertures 22, 24 and 26 in the dielectric layer 16, the cathode film 14 and the dielectric sheet 18, respectively, and the exposed anode 12 and cathode 14. Working area 20 allows the detection of hydrogen peroxide through a current related to glucose concentration. In the reaction to be measured, oxidation of hydrogen peroxide is done at the platinum anode 12. Hydrogen peroxide is produced through catalytic reaction of glucose and oxygen with an enzyme such as glucose oxidase.

In the preferred electrode 10, a layer of enzyme 28 (FIG. 5),such as glucose oxidase, is bonded or immobilized on anode 12 at the working area 20. To allow passage of glucose and oxygen to the enzyme 28 and to block passage of other contaminants, a glucose permeable membrane 30 is bonded over the enzyme layer 28 and to the working area 20. Preferably, membrane 30 is a silicone water-based elastomer of the type described in the copending application Serial No. 749,724 filed June 28, 1985.

In accordance with an important feature of the present invention it has been found that a dispersion of a polymerizable silicon-containing compound applied in an incompletely cured form as a silicon compound dispersed phase in a liquid carrier, the carrier being essentially insoluble in the dispersed phase and removable from the dispersion during curing, will dry and cure as a continuous layer, film or membrane having unexpectedly high glucose-permeability to function as a single membrane 30. The silicon-containing compound can be dispersed in the continuous phase as a monomer, oligomer, prepolymer, or incompletely cured polymer. The silicon compound is cured in place as a continuous polymeric coating or layer. The removable carrier removed during curing, such as by volatilization, should be included in an amount of at least 5% by weight of the dispersion, and preferably 10-90% by weight.

It has been found that the polymerizable silicon-containing compounds including monomers, oligomers, prepolymers, and incompletely cured polymers or mixtures thereof capable of polymerization or further polymerization in dispersed form will form cured layers or membranes when cured or polymerized in a dispersed layer upon removal of the continuous phase during curing to provide a layer or membrane having unexpectedly good oxygen and glucose-permeability without allowing the passage of electrode-sensitive interferents therethrough. The polymerizable siliconcontaining compounds, after dispersion in a continuous phase, such as by including an emulsifier, can be cured in any known manner during removal of the continuous phase, such as by evaporation of water from a water-continuous phase silicon emulsion or dispersion, as disclosed in the Johnson et al Patent No. 4,221,688, incorporated herein by reference, or as disclosed in Elias Patent No. 4,427,811, also incorporated herein by reference. Further, the dispersion of the silicon-containing compound can include a suitable curing catalyst or can be heat cured so long as the dispersion of the polymerizable silicon-containing compound is applied as a layer in the form of an incompletely cured dispersion and at least a portion of the carrier or continuous phase is removed from the dispersion during final curing. Without being limited to any particular mechanism, it is theorized that some alignment of the aggregating or polymerizing silicon-containing polymer molecules, during polymerization, occurs during final removal of the carrier to form micells such that the aggregating silicon-containing polymer molecules are bound upon curing in a manner capable of permitting the permeation of glucose and oxygen between molecules while excluding electrode-sensitive interferants.

The silicon-containing compounds, useful in accordance with the invention are those which can be dispersed in an essentially insoluble liquid carrier, such as water, are polymerizable in the dispersed form, and result in a continuous film or layer upon curing.

In accordance with one embodiment of the present invention, the polymerizable siliconcontaining compound is an organosiloxane, and particularly a diorganosiloxane comprising essentially a linear species of repeating diorganosiloxane units which may include small numbers of monoorganosiloxane units up to a maximum of about one monoorganosiloxane unit for each 100 diorganosiloxane units wherein the polymer chain is terminated at each end with silicone-bonded hydroxyls, as disclosed in Johnson et al. U.S. Pat. No. 4,221,688, hereby incorporated by reference.

In accordance with another important embodiment of the present invention, the polymerizable silicon-containing compound forming a glucosepermeable membrane is applied onto an electrode as an aqueous silicone emulsion comprising a continuous water phase and an anionically stabilized dispersed silicone phase wherein the silicone phase is a graft copolymer of a water soluble silicate and a hydroxyl endblocked polydiorganosiloxane. As disclosed in the Saam Patent No. 4,244,849, such silicon emulsions having a pH within the range of from 8.5 to 12, are stable upon extended storage and result in a cured elastomeric continuous layer upon removal of water under ambient conditions. These silicone compounds are obtained from the interaction of hydroxyl end-blocked polydiorganosiloxanes and alkali metal silicates to form graft copolymers anionically stablized in aqueous emulsions at a pH of, for example, 8.5 to 12. If stability is not important, however, the pH is not critical. For example, the emulsion can be applied in layer form to manufacture the membrane as soon as the components are homogeneously dispersed.

The expression "hydroxyl endblocked polydiorganosiloxane" is understood to describe an essentially linear polymer of repeating diorganosiloxane units containing no more than small impurities of monoorganosiloxane units. The hydroxyl endblocked diorganosiloxane will therefore have essentially two silicon-bonded hydroxyl radicals per molecule. To impart elastomeric properties to the product obtained after removal of the water from the emulsion, the polysiloxane should have a weight average molecular weight ($M_w$) of at least 5,000. Polysiloxanes with weight average molecular weights below 5000, for example down to about 90, also are useful so long as the polymers form a continuous film or layer upon curing. Tensile strengths and elongations at break improve with increasing molecular weight with relatively high tensile strengths and elongations obtained above 50,000 $M_w$. However, since in a preferred embodiment of the invention, the cured polymers are bonded directly to an electrode and do not undergo any severe mechanical stress during use, high strength is not necessary for the polymer to be useful in the invention described herein. The maximum $M_w$ is one which can be emulsified or otherwise dispersed in a liquid carrier or continuous phase, such as water. Weight average molecular weights up to about 1,000,000 for the incompletely cured dispersed polysiloxane are expected to be practial for this invention. Upon curing, there is no upper limit to the molecular weight of the membrane. The preferred $M_w$ for the polymerizable dispersed siloxane is in the range of 1,000 to 700,000.

Organic radicals on useful hydroxyl endblocked polydiorganosiloxanes can be, for example, monovalent hydrocarbon radicals containing less than seven carbon atoms per radical and 2-(perfluoroalkyl)ethyl radicals containing less than seven carbon atoms per radical. Examples of monovalent hydrocarbon radicals include methyl, ethyl, propyl, butyl, isopropyl, pentyl, hexyl, vinyl, cyclohexyl and phenyl and examples of 2-(perfluoroalkyl)ethyl radicals include 3,3,3-trifluoropropyl and 2-(perfluorobutylmethyl). The hydroxyl endblocked polydiorganosiloxanes preferably contain organic radicals in which at least 50 percent are methyl. The preferred polydiorganosiloxanes are the hydroxyl endblocked polydimethylsiloxanes.

In accordance with one important embodiment of the present invention, the hydroxyl endblocked polydiorganosiloxane is employed as an anionically stabilized aqueous emulsion. For the purposes of this embodiment "anionically stabilized" means the polydiorganosiloxane is stabilized in emulsion with an anionic surfactant. The most preferred anionically stabilized aqueous emulsion of hydroxyl endblocked polydiorganosiloxane are those prepared by the method of anionic emulsion polymerization described by Findlay et al. in U.S. Pat. No. 3,294,725 hereby incorporated by reference to show the methods of polymerization and to show anionically stabilized emulsions of hydroxyl endblocked polydiorganosiloxanes. Another method of preparing hydroxyl endblocked polydiorganosiloxanes is described by Hyde et al in U.S. Pat. No. 2,891,920, hereby incorporated by reference to show the hydroxyl endblocked polydiorganosiloxanes and their method of preparation. These methods and others are known in the art.

An alkali metal silicate or colloidal silica can be included in the emulsified silicone composition for the preparation of extended storage stable emulsions used in the invention. The alkali metal silicates preferred for use in the emulsions forming the glucose-permeable membranes of the present invention are water soluble silicates. The alkali metal silicate is preferably employed as an aqueous solution. Aqueous silicate solutions of any of the alkali metals can be employed such as lithium silicate, sodium silicate, potassium silicate, rubidium silicate and cesium silicate.

The colloidal silicas are well known in the art and many are commercially available and can be included in the dispersion for increased strength and storage stability. Although any of the colloidal silicas can be used including fumed colloidal silicas and precipitated colloidal silicas, the preferred colloidal silicas are those which are available in an aqueous medium. Colloidal silicas in an aqueous medium are usually available in a stabilized form, such as those stabilized with sodium ion, ammonia or an aluminum ion. Aqueous colloidal silicas which have been stabilized with sodium ion are particularly useful for forming an emulsion because the pH requirement can be met by using such a sodium ion stabilized colloidal silica without having to add additional ingredients to bring the pH within the range of, for example, 8.5 to 12. The term "colloidal silica" as used herein are those silicas which have particle diameters of from 0.0001 to 0.1 micrometers. Preferably, the particle diameters of the colloidal silicas are from 0.001 to 0.05 micrometers.

The colloidal silica can be added to the anionically stabilized hydroxylated polydiorganosiloxane in the form of a dry powder or as an aqueous dispersion. The best method is to add the colloidal silica in the form of a sodium ion stabilized aqueous dispersion of colloidal silica. There are many such sodium ion stabilized aqueous dispersions of colloidal silica which are commercially available. These commercial colloidal silicas are usually available in aqueous dispersions having from 15 to 30 weight percent colloidal silica and having a pH in the range of 8.5 to 10.5.

Aqueous solutions of sodium or potassium silicate are well known and are commercially available. The solutions generally do not contain any significant amount of discrete particles of amorphous silica and are commonly referred to as water glass. The ratio by weight of $SiO_2$ to alkali metal oxide in the aqueous solutions of alkali metal silicates is not critical and can be varied within the usual range of about 1.5 to 3.5 for the sodium silicates and 2.1 to 2.5 for the potassium silicates. The aqueous alkali metal silicate solutions are particularly useful in preparing the emulsions of the present invention because the addition of the silicate solution often brings the pH of the emulsion within the range of about 8.5 to about 12 so that additional ingredients are not necessary to adjust the pH of the emulsion. Of course, other aqueous alkali metal silicate solutions such as those prepared by hydrolyzing silicon esters in aqueous alkali metal hydroxide solutions can also be employed in the present invention.

In accordance with one embodiment of the present invention, the polymerizable silicon-containing compound is dispersed by combining an aqueous solution of an alkali metal silicate and the polymerizable silicon-containing compound in an emulsion so that a graft copolymer is formed as dispersed particles. The preferred procedure for preparing silicone emulsions is to add the alkali metal silicate to an anionically stabilized aqueous emulsion of one or more hydroxyl endblocked polydiorganosiloxanes, adjust the pH of the emulsion within the range of about 8.5 to 12 and then age the emulsion for a time period such that an elastomeric product is formed upon removal of the water under ambient conditions. In this embodiment, the pH of the emulsion containing dissolved silicate and dispersed hydroxyl endblocked polydiorganosiloxane is important to the formation of the emulsion. A pH of 8.5 to 12 maintains the alkali metal silicate dissolved so that sufficient graft copolymerization between the dissolved silicate and dispersed siloxane occurs during removal of the carrier (e.g. water) to produce an emulsion capable of providing polymerization or further polymerization of the silicon-containing compound when deposited as a layer to form a membrane. If the pH is lower than the stated range, silicic acid is formed from the alkali metal silicate. Silicic acid is unstable and rapidly polymerizes by condensation which can gel the emulsion. Since silicic acid formation is almost completely suppressed at a pH of 10 to 12 and the reaction between dissolved alkali metal silicate and dispersed siloxanes occurs more rapidly within the pH range of 10–12, this pH range is preferred for emulsions containing an alkali metal silicate.

Silicone emulsions prepared by this silicate copolymerization embodiment are aged at a pH range of 8.5 to 12 for a time period sufficient to allow interaction between the dissolved silicate and the dispersed siloxane so that an elastomeric product is formed upon removal of the water under ambient conditions, as disclosed in Saam U.S. Pat. No. 4,244,849, hereby incorporated by reference. The aging period is effectively reduced when an organic tin salt is employed in an amount of about 0.1 to 2 parts by weight for each 100 parts by weight of polydiorganosiloxane. The organic tin salts expected to be useful in the emulsions include mono-, diand triorganotin salts. The anion of the tin salt employed is not critical and can be either organic or inorganic although organic anions such as carboxylates are generally preferred. Organic tin salts that can be employed include octyltin triacetate, dioctyltin dioctoate, didecyltin diacetate, dibutyltin diacetate, dibutyltin dibromide, dioctyltin dilaurate and trioctyltin acetate. The preferred diorganotin dicarboxylate is dioctyltin dilaurate.

The concentration of the polymerizable silicon-containing compound, e.g. the hydroxyl endblocked polydiorganosiloxane in the stabilized emulsion is not critical particularly since the water or other continuous phase carrier is removed during curing of the Si phase during film, layer or membrane formation.

The relative amounts of alkali metal silicates and hydroxyl endblocked polydiorganosiloxane employed can vary over a considerable range. Preferred elastomer properties are obtained when 0.3 to 30 parts by weight silicate is employed for each 100 parts by weight siloxane.

Other useful polymerizable silicon-containing compounds for forming the dispersions useful in forming a continuous silicon-containing polymer membrane having glucose-permeability in accordance with the present invention include the vinyl endblocked polydiorganosiloxanes dispersed together with an organosilicone compound having silicone-bonded hydrogen atoms, as disclosed in the Willing Patent No. 4,248,751 hereby incorporated by reference. As disclosed in the Willing patent, these silicone compounds are generally dispersed by emulsifying the vinyl endblocked polydiorganosiloxane together with an organosilicone compound having silicon-bonded hydrogen atoms using water and a surfactant to form an emulsion and thereafter adding a platinum catalyst and heating the emulsion to form a crosslinked silicone.

The vinyl endblocked polydiorganosiloxane can be any of the polydiorganosiloxanes endblocked with diorganovinylsiloxy units and can be represented by the formula $(CH_2=CH)R_2SiO(R_2SiO)_xSiR_2(CH=CH_2)$ where each R is a monovalent hydrocarbon radical or a monovalent halogenated hydrocarbon radical and x is a representation of the number of repeating diorganosiloxane units in the polymer. The monovalent radicals can be any of those known in the art, but are preferably those with six carbon atoms or less. The preferred polydiorganosiloxanes are those wherein the monovalent organic radicals are methyl, ethyl, phenyl, 3,3,3,-trifluoropropyl and mixtures thereof wherein at least 50 percent of the radicals are methyl radicals. The polydiorganosiloxane can be a single type polymer with the same kind of repeating diorganosiloxane units or with a combination of two or more kinds of repeating diorganosiloxane units, such as a combination of dimethylsiloxane units and methylphenylsiloxane units. A mixture of two or more polydiorganosiloxanes also is useful. The value of x is not critical since upon final curing in the dispersed layer, the value of x increases rapidly. The upper limit of polydiorganosiloxane which is suitable for this invention is limited only to the extent that it cannot be dispersed to form a homogenous dispersion to achieve a homogenous layer capable of forming a continuous membrane upon complete curing.

In accordance with this vinyl-endblocked embodiment, the organosilicone compound or mixture of compounds dispersed with the polydiorganosiloxane is one which contains silicon-bonded hydrogen atoms. The organosilicon compound can be any compound or combination of compounds containing silicon-bonded hydrogen atoms useful as crosslinkers and providing an average of silicon-bonded hydrogen atoms per molecule of organosiloxane compound of at least 2.1. Such organosilicon compounds are known in the art as illustrated in U.S. Pat. No. 3,697,473 which is hereby incorporated by reference. The preferred organosilicon compounds are those which are siloxanes made up of units selected from $HSiO_{1.5}$, $R'HSiO$, $R'_2HSiO_{0.5}$, $R'SiO_{1.5}$, $R'_2SiO$, $R'_3SiO_{0.5}$ and $SiO_2$ such that there is at least 2.1 silicon-bonded hydrogen atoms per molecule. Each R' is preferably selected from an alkyl radical of 1 to 12 carbon atoms inclusive, phenyl and 3,3,3-trifluoropropyl.

The amount of vinyl endblocked diorganosiloxane and organosilicon compound can vary broadly in weight amounts because the unit of weight for each vinyl radical or silicon-bonded hydrogen atom will vary considerably. Such "units of weight" are determined by dividing the molecular weight by the number of vinyl radicals per molecule or number of SiH per molecule. Because the cross-linked molecules in the membrane are formed by the reaction between the vinyl radical of the polydiorganosiloxane and the silicon-bonded hydrogen atom (SiH) of the organosilicon compound, the amounts of each will depend upon the ratio of SiH to vinyl. The stoichiometry would suggest that about one SiH per vinyl is all that is needed, however, the reactivity of the SiH can vary significantly, as well as its availability for reaction. For this reason, the ratio of SiH to vinyl can vary beyond the stoichiometric amounts and still provide products capable of polymerizing in layer form to provide continuous glucose-permeable membranes. The vinyl endblocked polydiorganosiloxane and organosilicon compound preferably are combined such that the ratio of SiH to vinyl can vary from 0.75/1 to 4/1, with the most preferred range of 0.75/1 to 1.5/1.

The platinum catalyst can be any of the platinum catalysts known to catalyze the addition of silicon-bonded hydrogen atoms to silicon-bonded vinyl radicals. Platinum catalysts can be any of the known forms, ranging from platinum as such or as deposited on carriers such as silica gel or powdered charcoal, to platinic chlorides, salts of platinum and chloroplatinic acid. The dispersibilty of the platinum catalysts in the siloxane can be increased by complexing it with vinyl-containing siloxanes such as described in U.S. Pat. No. 3,419,593.

The amount of platinum catalyst used should be such that there is at least 0.1 part by weight platinum per one million parts by weight of the combined weight of polydiorganosiloxane and organosilicon compound. Preferably, the amount of catalyst used is from 1 to 20 parts by weight platinum per million parts by weight of polydiorganosiloxane and organosilicon compound. Larger amounts of platinum can be used if economic considerations are not important.

For those cases where a platinum catalyst is included in the dispersion and a platinum catalyst inhibitor is desired to prevent complete curing prior to layering the dispersion for formation of the membrane, there are many types of known inhibitors. These inhibitors retard or inhibit the activity of the platinum catalyst, but allow the platinum catalyst to become active at elevated temperatures, such as above 70° C. If the carrier in the dispersion is water, the selection of an inhibitor should be one which does not have its effectiveness destroyed by water or surfactants or it does not destroy the emulsion. Effective inhibitors include the acetylenic alcohols and other acetylenic compounds described in U.S. Pat. No. 3,445,420. Other platinum catalyst inhibitors are known as defined in U.S. Pat. No. 3,188,299, U.S. Pat. No. 3,188,300, U.S. Pat. No. 3,192,181, U.S. Pat. No. 3,344,111, U.S. Pat. No. 3,383,356, U.S. Pat. No. 3,453,233, U.S. Pat. No. 3,453,234 and U.S. Pat. No. 3,532,649. The dispersed composition can be heated for a period of time to partially cross-link the Si-containing compounds to form a stable emulsion of cross-linked particles dispersed in a carrier. After application in layer form on an electrode, the layer further cures to form a continuous, glucose permeable membrane.

Evaporation of the carrier may be assisted by a flow of dry air or other gas, either at ambient temperature or at an elevated temperature, by infrared heating or a combination of the various means. Care should be taken when accelerated means are used to evaporate the carrier, e.g. water, that the rapidly leaving water vapor does not produce undesirable discontinuities in the film.

Other reinforcing materials useful for increasing the structural integrity of the cured glucose-permeable membranes of the present invention include the copolymers disclosed in the Huebner et al Patent No. 4,288,356 hereby incorporated by reference. The copolymers are emulsion polymerized and comprise free radical polymerized monomers selected from at least one unsaturated organic monomer and at least one unsaturated organosilicone monomer. The copolymers are made from 1 to 7 weight percent unsaturated organosilicon monomer and from 93 to 99 weight percent organic monomer. It is believed that any of the unsaturated organic monomers commonly used to form polymers through free radical polymerization can be used either by themselves or in combination; for example, styrene, methylmethacrylate, and vinyl chloride. The unsaturated organosilicon monomer can be an unsaturated silane, siloxane, or silazane that will copolymerize with the unsaturated organic monomer or mixture of unsaturated organic monomers used and will form $\equiv$ SiOH under the conditions of an emulsion polymerization method used to produce the copolymer.

The unsaturated organosilicon monomer can be a silane of the formula $R'R''_xSi(R''')_{3-x}$ where $R'$ is an olefinic unsaturated radical such as vinyl, allyl, acryloxypropyl, or methacryloxypropyl, $R''$ is an alkyl radical containing 1 to 4 inclusive carbon atoms or a phenyl radical, and $R'''$ is a hydrolyzable group such as $-OR''$, $-OCOR''$, or halogen, and x is 0, 1 or 2. The unsaturated organosilicon monomer can be a cyclic siloxane of the formula $(R'R''SiO)_a$ where $R'$ and $R''$ are as defined and a is from 3 to 6 inclusive. The unsaturated organosilicon monomer can be a disilazane of the formula $R'R''_2Si-NH-SiR''_2R'$ where $R'$ and $R''$ are as defined. The unsaturated organosilicon monomer can be a cyclic silazane of the formula $(R'R''SiNH)_3$ where $R'$ and $R''$ are as defined. A preferred unsaturated organosilicon monomer is vinyltriethoxysilane.

Examples of unsaturated organosilicon monomers include silanes such as $ViMeSiCl_2$, $ViMe_2SiOMe$, $ViMeSi(OEt)_2$, and $ViSi(OEt)_3$, siloxanes such as $(ViMe_2Si)_2O$, $(ViMeSiO)_3$, and $(ViMeSiO)_a$ where a is 3 to 6 inclusive, and silazanes such as $(ViMe_2Si)_2NH$ and $(ViMeSiNH)_3$ where Me is methyl radical, E is an ethyl radical and Vi is vinyl radical.

The unsaturated organic monomer and the unsaturated organosilicon monomer can be emulsion polymerized by the common methods of performing such copolymerizations. One such process is described by Blackderf in U.S. Pat. No. 3,706,697 which is hereby incorporated by reference to show a process for copolymerizing an acrylic ester and an acryloxyalkylalkoxysilane by emulsion polymerization of the organic monomer through a free radical generator.

For example, a mixture is prepared of water and an anionic surfactant, and then a mixture of styrene and vinyltriethoxysilane is slowly added under a nitrogen blanket. Ammonium persulfate then is added as the polymerization catalyst. Heating the mixture initiates the polymerization, but it is also necessary to control the reaction temperature so that the emulsion does not overheat due to the exothermic reaction. After polymerization, the emulsion is adjusted to a pH of greater than 7.

The copolymer is added in an amount of 5 to 100 parts by weight of the emulsion polymerized copolymer for each 100 parts by weight of polymerizable Si-containing compound, e.g. polydiorganosiloxane. The addition of the copolymer serves to act as a reinforcement or filler for the polydiorganosiloxane. Amounts of from 5 to 25 parts of copolymer added per 100 parts of polymerizable Si-containing compound yield a reinforced membrane having the desired glucose-permeability and strength without the addition of other fillers such as $SiO_2$. When the amount of copolymer added is from 25 to 60 parts by weight, the final product obtained by drying the emulsion is a higher strength membrane. The more copolymer added, the harder and less elastic the final membrane becomes.

In accordance with one embodiment of the invention, an alkyl tin salt is added to the dispersion to catalyze the curing of the final emulsion during the devolatilization or other removal of the carrier to yield the cured membrane. Preferred salts are dialkyltin dicarboxylates such as dibutyltindiacetate, dibutyltindilaurate, and dioctyltindilaurate. Most preferred is dibutyltindilaurate. The emulsion of catalyst is used in an amount sufficient to yield from 0.1 to 2 parts by weight of the alkyl tin salt for each 100 parts by weight of the polymerizable Sicontaining compound, e.g. polydiorganosiloxane.

Larger amounts could be used, but the larger amount would serve no useful purpose.

A silane cross-linking agent, of the general formula $A_m\text{-Si(OR)}_{4-m}$ can be added to the dispersion to enhance the physical properties of the cured membrane. The radical A, in the silane cross-linking agent is a member selected from the group consisting of a hydrogen atom, monovalent hydrocarbon radicals containing 1 to 6 inclusive carbon atoms, and monovalent halohydrocarbon radicals containing 1 to 6 inclusive carbon atoms. Preferred radicals are methyl, ethyl, phenyl, and 3,3,3-trifluoropropyl with methyl being most preferred. The radical R is a hydrogen atom, and alkyl group containing 1 to 4 inclusive carbon atoms, $-CH_2CH_2OH$, $-CH_2CH_2OCH_3$, or a $-CH_2C-H-2OC_2H_5$ group. The R radicals on a silane molecule can be the same or different. The number of A radicals can be 0 or 1, meaning that a silane molecule can be either tri or tetra-functional in order to function as a crosslinker in the curing of the final membrane of this invention. The OR group on the silane is a hydrolyzable group that forms =SiOH during curing of the membranes of this invention. The preferred silane cross-linking agent is methyltrimethoxysilane. The silane cross-linking agent can be included in a sufficient amount to obtain the desired degree of crosslinking. The amount to be used depends upon the hydroxyl content of the polymerizable Si-containing compound and the molecular weight of the crosslinking agent chosen. The more crosslinking agent used, the harder and less elastic the membrane becomes. Useful amounts of the preferred methyltrimethoxysilane crosslinker vary from 1 to 7 parts by weight of silane per 100 parts by weight of polydiorganosiloxane.

Other useful silicone containing compounds capable of polymerizing to form a membrane, film or layer that is glucose-permeable include the copolymers of diorganosiloxanes and any hydrolyzable silane, as disclosed in the Sorkin Patent No. 3,624,017, hereby incorporated by reference.

The diorganosiloxanes can be included in the dispersion as a monomer or a polymer. The monomer can be partially polymerized in the dispersion or emulsion and then silane added and copolymerized with the diorganosiloxane polymer. The surfactant used to form an emulsion with the copolymers can be either anionic, cationic or nonionic and any catalyst useful to initiate the copolymerization can be used, such as a strong acid or a strong base. The starting diorganosiloxane can be either a cyclic or a linear material and the molecular weight of the starting diorganosiloxane is not critical.

The dispersion of the polymerizable silicon-containing compound or compounds can contain the components in a broad range of concentrations. The preferred concentration range will depend on the thickness of the membrane desired. For example, to provide a thick elastomeric membrane (0.5 mm thick) that does not form cracks as the carrier or continuous phase evaporates, it is best to use a dispersion having a combined amount of silicate and polydiorganosiloxane in the range of 67 to 160 parts by weight for each 100 parts by weight of carrier, e.g. water. Preferred membrane thicknesses are 0.073 to 0.64 mm (0.5 to 25 mils), for example 0.11 mm (4.5 mils).

If an emulsifying agent is incorporated into the composition to form the dispersion the amount of emulsifying agent can be less than 2 weight percent of the emulsion, and the emulsifying agent can result from neutralized sulfonic acid used in the emulsion polymerization method for the preparation of a hydroxyl endblocked polydiorganosiloxane.

Anionic surfactants are preferably the salt of the surface active sulfonic acids used in the emulsion polymerization to form the hydroxyl endblocked polydiorganosiloxane as shown in U.S. Pat. No. 3,294,725, hereby incorporated by reference to show the surface active sulfonic acids and salts thereof. The alkali metal salts of the sulfonic acids are preferred, particularly the sodium salts. The sulfonic acid can be illustrated by aliphatically substituted benzenesulfonic acids, aliphatically substituted naphthalene sulfonic acids, aliphatic sulfonic acids, silylalkylsulfonic acids and aliphatically substituted diphenylethersulfonic acids. Other anionic emulsifying agents can be used, for example, alkali metal sulforicinoleates, sulfonated glyceryl esters of fatty acids, salts of sulfonated monovalent alcohol esters, amides of amino sulfonic acid such as the sodium salt of oleyl methyltauride, sulfonated aromatic hydrocarbon alkali salts such as sodium alpha-naphthalene monosulfonate, condensation products of naphthalene sulfonic acids with formaldehyde, and sulfates such as ammonium lauryl sulfate, triethanol amine lauryl sulfate and sodium lauryl ether sulfate.

Nonionic emulsifying agents also can be included in the emulsion in addition to the anionic emulsifying agents. Such nonionic emulsifying agents are, for example, saponins, condensation products of fatty acids with ethylene oxide such as dodecyl ether of tetraethylene oxide, condensation products of ethylene oxide and sorbitan trioleate, condensation products of phenolic compounds having side chains with ethylene oxide such as condensation products of ethylene oxide with isododecylphenol, and imine derivatives such as polymerized ethylene imine.

The polymerizable silicon-compound dispersion used to form the glucose-permeable membranes of the present invention can contain additional ingredients to modify the properties of the dispersions or the cured polymeric membrane products obtained from the dispersion. For example, a thickener can be added to modify viscosity of the dispersion or to provide thixotropy for the dispersion. An antifoam agent can be added to the dispersion to reduce foaming during preparation, coating or curing in layer form.

Fillers can be added to the dipsersion to reinforce, extend or pigment the membrane. Useful fillers include colloidal silica, carbon black, clay, alumina, calcium carbonate, quartz, zinc oxide, mica, titanium dioxide and others well known in the art. These fillers should be finely divided and it may be advantageous to use aqueous dispersions of such fillers if they are commercially available, such as aqueous dispersions of carbon black. The polymerizable Si-compound containing dispersions do not require a filler and such can be added in dry or aqueous forms to provide selected properties to the membrane.

The filler preferably has an average particle diameter of less than 10 micrometers. Useful fillers have had average particle diameters ranging down to as low as 0.05 micrometers. When these silicone emulsions are spread out for final curing to form the glucose-permeable membranes of the present invention, the water or other nonsolvent carrier evaporates, or is otherwise removed, to leave a cured glucose and oxygenpermeable membrane. Evaporation of the carrier is usually complete within a few hours to about one day depending on the dispersion film thickness and method of application. Another of the important advantages of the present invention is the excellent adhesion shown by these membranes for both polar and non-polar substrates.

It should be understood that this invention is not limited to removal of continuous liquid phase in the silica dispersion by evaporation, since other methods such as coagulation may be useful. Heating the polymerizable silicon-containing compound dispersions to more rapidly remove the carrier to produce more rapidly cured membranes also may be advantageous.

In accordance with the present invention, the glucose-permeable membranes 30 disclosed herein are useful in conjunction with any known method and apparatus for measuring the concentration of glucose permeating the membrane. More specifically, glucose concentrations have been determined amperometrically using soluble glucose oxidase held between Cupropane membranes or physically entrapped in a polyacrylamide gel coated onto an oxygen electrode. The decrease in oxygen pressure is equivalent to the glucose content in the biological fluid, such as blood or plasma, in accordance with the reaction:

Instead of measuring the decrease in oxygen content, the hydrogen peroxide produced in the enzymatic reaction using a platinum electrode is an alternative use for the glucose-permeable membrane. Such a platinum electrode device for measuring the hydrogen peroxide is disclosed in the Clark U.S. Pat. No. 3,539,455.

Some presently existing apparatus uses glucose oxidase held on a filter trap and utilizes two platinum electrodes, one to compensate for any electrooxidizable compounds in the sample, such as ascorbic acid, and the second to monitor the enzyme reaction producing the hydrogen peroxide. Others also have used quinone as the hydrogen accepter in place of oxygen and measure the electro oxidation of quinone in accordance with the reaction:

(E = 0.4 V vs. standard calomel electrode)

In such a quinone electrooxidation, glucose oxidase is trapped in a porous gelled layer and covered with a dialysis membrane over a platinum electrode. Others have immobilized glucose oxidase onto a platinum-glass electrode held in place by cellophane. The current produced is proportional to the glucose concentration. Others have measured the local decrease in iodide activity at an electrode surface either in a flow stream or at a stationary electrode in accordance with the following catalyzed reactions:

While, in the prior art, such an electrode measurement of glucose required removal of interferring reducing agents, such as ascorbic acid, the glucose-permeable membranes of the present invention are very selective to permeation of glucose and oxygen while preventing the permeation of electrode sensitive reducing agents. Accordingly, the membranes of the present invention are also very well suited to such electrode measurement systems.

One of the more important advantages to the glucose-permeable membranes of the present invention, however, is the capability of these membranes to be bonded to an electrode activated with a bonded layer of a suitable catalyst, such as glucose oxidase, or glucose dehydrogenase to eliminate any necessity for any intermediate layer of ion-conducting buffer solution. In accordance with this embodiment of the present invention a compound capable of catalyzing the reaction of glucose with oxygen is bonded directly to the electrode 10, e.g. the anode 12, and the glucose-permeable membrane 30 of the present invention is coated over the catalyzed anode 12 to entrap the catalyst 28 between the membrane layer 30 and the anode 12 outer surface. The catalyst e.g. glucose oxidase 28, is immobilized on the outer surface of the electrode 10 in any suitable manner.

Immobilization of enzyme 28 directly on anode 12 can be accomplished in several ways known in the art. For example, immobilization can be accomplished through a silane coupling agent such as N-beta-aminoethyl-gamma-aminopropyltrimethoxy silane. An important characteristic of silane coupling agents is their ability to form covalent bonds with many metal oxides and hydroxylated metal surfaces at the Si(OR$_3$) portion of the silane molecule. This is true with platinum. Upon normal exposure to ambient conditions, platinum readily develops an hydroxy functional surface. An alkoxysilane rapidly reacts with this surface to form stable "Pt—O—Si" bonds. The silane coupling agents also include an organofunctional, e.g. amino, group that reacts with the catalyst, such as glucose oxidase 28, via a suitable crosslinking agent, such as glutaraldehyde, to immobilize the oxidizing enzyme, e.g. glucose oxidase 28, directly onto the anode 12 and the bonded enzyme 28 remains active for several months.

To achieve the full advantage of the present invention, the catalyst 28 capable of catalyzing the reaction of glucose with oxygen is immobilized on the surface of the anode 12 using a silane coupling agent and a suitable crosslinking agent. Crosslinking agents suitable for immobilizing a protein catalyst such as glucose oxidase to a platinum surface of an electrode include glutaraldehyde, cyanogen bromide, hydrazine, benzoquinone, periodate, trichloro-s-triazine, tosyl chloride and diazonium. Each of these crosslinking agents is suitable for immobilization of proteins such as glucose oxidase by coupling to a primary amino functional silane coupling agent, with the exception of the diazonium which is couplable to a phenol or aromatic amine functional silane coupling agent. Further, the trichloro-s-triazine cross-linking agent can crosslink the enzyme through a hydroxyl functional group of a silane coupling agent and tosyl chloride is couplable to a thiol functional group of a silane coupling agent. Some of the suitable silane coupling agents include 3-aminopropyltriethoxysilane; N-2-aminoethyl-3-aminopropyltrimethoxysilane; 4-aminobutyldimethylmethoxysilane; (aminoethylaminomethyl)phemethyltrimethoxysilane; 4-aminobutyltriethoxysilane; N-(2-aminoethyl)-3-aminomethyldimethoxysilane; and 3-aminopropyltris(-trimethylsiloxy)silane and the like.

Once the catalyst 28 has been bonded to the anode 12, the membrane 30 is applied over the enzyme 28 in working area 20. The membrane materials described herein are very compatible with whole blood, have a durable surface and are highly selective to oxygen penetration so that a sufficient stoichiometric excess of oxygen permeates the membrane 30 even from whole blood.

A surprising characteristic of the polymerized silicon-containing membrane 30 is glucose-permeability which is contrary to the teaching of the prior art.

Another surprising characteristic of the membrane 30 is its ability to prevent passage of abscorbic acid to electrode 10. Absorbic acid is a major interferent and is essentially prevented from reaching the electrode surface 12 by membrane 30. Further, the cured membrane 30 has a durable and resilient surface allowing the membrane 30 to be rinsed and wiped off after use to remove any contaminents that could build up and foul the membrane.

The preferred materials for membrane 30 are an anionically stabilized, water-based hydroxyl endblocked polydimethylsiloxane elastomer containing about 5 percent by weight colloidal silica sold by Dow Corning as elastomer and manufactured in accordance with Dow Corning U.S. Pat. No. 4,221,668. To show the new and unexpected results using membranes 30 formed from a dispersion of polymerizable silicon-containing compounds applied in layer form in an incompletely cured state dispersed in a removable liquid carrier, four membranes were made-three from silicone-water liquid dispersions and one from a silicone paste material having essentially no removable liquid phase. The membranes were prepared by casting the elastomers onto a polyester film with a 0.25 mm (10 mil). doctor blade and curing at ambient conditions. The three compositions having a removable carrier (water) were applied as neat polysiloxane emulsions. Curing was accomplished in 30-60 minutes but can be accelerated with heat. This process gave a final dry film (membrane) thickness of approximately 0.11 mm (4.5 mils).

The three carrier-removable silicone latex compositions from Dow Corning differ only slightly in material composition. Dow Corning 3-5024 is the base system containing hydroxyl endblocked dimethylpolysiloxane elastomer with 5 percent by weight $SiO_2$, and an anionic emulsifier and may also include a suitable cross-linking agent such as a silane and catalyst, such as an alkyl tin salt. This material is the least viscous (1000 cps) of the three and cures to a thin clear film.

A second silicone water based elastomer, Dow Corning 3-5025, identical to Dow Corning 3-5024 with the addition of an organic, thixotropic additive, has a pre-cured viscosity of 25000 cps. This film is also clear on drying.

A third silicone water based elatomer, Dow Corning 3-5035, includes about 4.5 percent by weight $TiO_2$ filler. These films are opaque and white in color.

A heat-curable silicone paste (Dow Corning 3-9595) having essentially no volatizable carrier was also tested for comparison purposes. Dow Corning 3-9595 is a dimethylpolysiloxane elastomer containing 40 percent by weight silica and is supplied as a two-part putty-like material requiring the material to be spread into a layer using a doctor blade.

Results of the evaluation of membranes made from the above-identified four materials are summarized in the following table:

| FLUX DENSITY (J) AND PERMEABILITY (P) OF SILICONE RUBBERS | | | | |
|---|---|---|---|---|
| MATERIAL | GLUCOSE | URIC ACID | ASCORBIC ACID | $H_2O_2$ |
| DC3-5024 Clear Latex | $J = 1.78 \times 10^{-11}$ $P = 7.31 \times 10^{-9}$ | $7.45 \times 10^{-14}$ $2.12 \times 10^{-10}$ | $5.79 \times 10^{-14}$ $2.04 \times 10^{-10}$ | $1.60 \times 10^{-12}$ $6.88 \times 10^{-9}$ |
| DC3-5025 Clear/ Latex | $J = 2.97 \times 10^{-11}$ $P = 1.22 \times 10^{-8}$ | $1.2 \times 10^{-12}$ $3.5 \times 10^{-9}$ | $4.6 \times 10^{-15}$ $1.6 \times 10^{-11}$ | $9.12 \times 10^{-13}$ $3.9 \times 10^{-9}$ |
| DC3-5035 White/ Latex | $J = 8.49 \times 10^{-11}$ $P = 3.49 \times 10^{-8}$ | $3.6 \times 10^{-12}$ $9.8 \times 10^{-9}$ | $6.9 \times 10^{-14}$ $2.5 \times 10^{-10}$ | $2.3 \times 10^{-11}$ $9.9 \times 10^{-8}$ |
| DC3-9595 putty consistency | $J = 7.41 \times 10^{-13}$ $P = 3.05 \times 10^{-11}$ | $1.5 \times 10x^{-14}$ $4.2 \times 10^{-11}$ | $3.8 \times 10^{-14}$ $1.4 \times 10^{-10}$ | $1.9 \times 10^{-13}$ $8.5 \times 10^{-10}$ |

J = flux density (moles $cm^{-2} sec^{-1}$)
P = permeability coefficient ($cm^2 sec^{-1}$)

Quite surprisingly, the glucose permeability of the silicone material in paste form having essentially no volatizable carrier is three orders of magnitude lower than Dow Corning 3-5025 and Dow Corning 3-5035 and two orders of magntidue lower than Dow Corning 3-5024. The evaluation table also emphasizes the three latex materials are much more selective for glucose relative to ascorbic acid than the paste form silicone.

Since laminated electrode 10 requires only a few molecular layers of platinum and silver or similar materials and membrane 30 requires very little material, electrode 10 is inexpensive. Further reducing the cost of electrode 10 is the method of fabrication. Referring to FIGS. 1-4, the method of fabricating electrode 10 is illustrated. The initial step involves fabricating apertures or holes 22, 24 and 26 in the dielectric layer 16 (FIG. 3), the cathode layer 14 (FIG. 2) and the dielectric sheet 18 (FIG. 1), respectively. Each of the dielectric sheet 18, cathode layer 14 and the dielectric layer 16 may be backed with adhesive such as silicone based adhesive with paper backing. The paper backing is peeled off and dielectric sheet 16, cathode layer 14 and dielectric layer 18 are laminated together and to the anode layer 12 by rollers 32 and 34 or a similar procedure. The membrane 30 is then applied in liquid form to the working areas 20 and allowed to cure. The resultant laminated strip is then cut by blades 36 and 38 to form individual electrodes 10.

It has been determined the adhesive backing functions as a dielectric and the adhesive backing on cathode layer 14 can be used to replace dielectric layer 16. This replacement further reduces the cost of electrode 10 by eliminating material and one assembly step. This also reduces the thickness of electrode 10 making it more planar and easier to apply the membrane 30.

Figure 1:
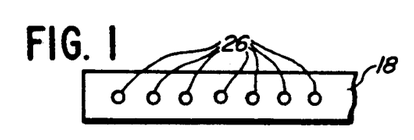
FIG. 1 is a top plan view of a dielectric top sheet prior to being laminated to form the electrode of the present invention.
Figure 2:
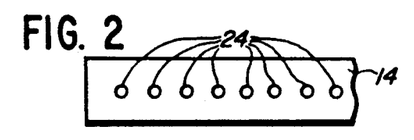
FIG. 2 is a top plan view of a silver foil or film prior to being laminated to form the electrode of the present invention.
Figure 3:
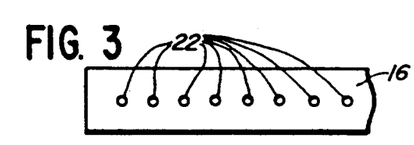
FIG. 3 is a top plan view of a dielectric middle sheet prior to being laminated to form the electrode of the present invention.
Figure 4:
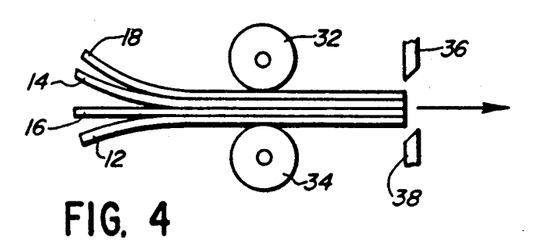
FIG. 4 is a schematic illustration of the step of laminating the top dielectric sheet, the silver foil or film and the middle dielectric sheet to platinum foil or film.
Figure 5:
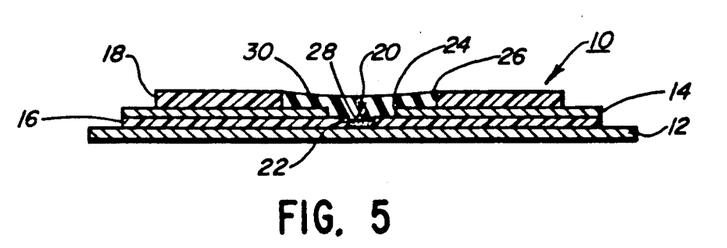
FIG. 5 is an enlarged, vertical cross sectional view of a laminated electrode constructed in accordance with the principles of the present invention.

Electrodes 10 can be configured in several different ways to provide for connection of the anode 12 and cathode 14 to electrical terminals or connectors that are coupled to an electronic readout in an electrochemical sensor. One configuration is illustrated in FIG. 5. Electrode 10 is configured in a stair step type of configuration with dielectric sheet 18 shorter than cathode 14. Cathode 14 is exposed and an electrical connection can be made to the upper surface. Anode 12 is exposed on the upper side and an electrical connection can easily be made.

Figure 6:
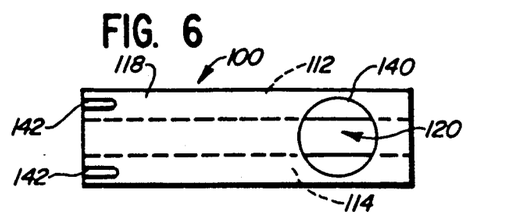
FIG. 6 is a top, plan view of an alternative embodiment of an electrode constructed in accordance with the principles of the present invention.

Another procedure for electrical connection is to form slots in the electrode. Referring to FIG. 6, an alternative electrode 100 is illustrated. Electrode 100 is substantially the same as electrode 10 except the anode 112 and cathode 114 are formed in strips or ribbons and positioned side by side. Working area 120 is defined by an aperture 140 extending through a top sheet 118 of dielectric material. To provide access for connection of terminals, slots 142 are formed in the top sheet 118 exposing anode 112 and cathode 114 allowing electrical connection. Slots 142 provide the advantage of allowing electrode 100 to be plugged into an electrochemical sensor with electrical contacts that slide onto the slots 142 making contact.

Figure 7:
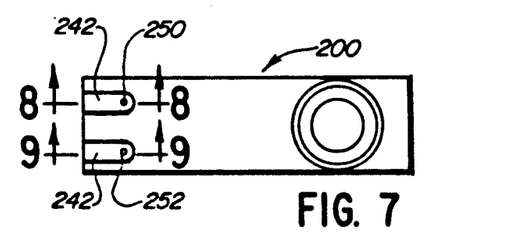
FIG. 7 is a top, plan view of a second alternative embodiment of an electrode constructed in accordance with the principles of the present invention.
Figure 8:
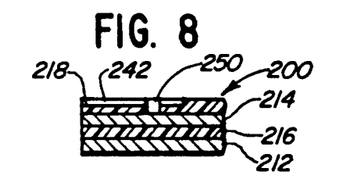
FIG. 8 is a view taken generally along line 8—8 in FIG. 7.
Figure 9:
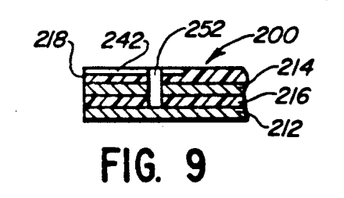
FIG. 9 is a view taken generally along line 9—9 in FIG. 7.

Another procedure for electrical connection is illustrated in FIG. 7. A second alternative electrode 200 is composed of the same elements as electrode 10 and includes an anode film 212, a layer 216 of dielectric material, a cathode film 214 and a top sheet 218 of dielectric material. Slots 242 can be formed in the top sheet 218 with a first hole 250 in top sheet 218 allowing access for an electrical contact pin to cathode 214. A second hole 252 can be fabricated in top sheet 218 and cathode 214 allowing access for a second electrical pin to the anode 212.

It is to be understood, several other configurations for electrical connection will connection be recognized by those skilled in the art and it is not intended to limit the present invention by the illustrated configurations.

In addition to vapor deposition, other procedures for forming the anode and cathode are contemplated. For example, the selected anode and cathode materials may be sputtered onto film or the materials may be silk screened onto a ceramic substrate. The examples mentioned are not intended to be limiting and other procedures known in the art are also contemplated.

By using vapor deposition and lamination technologies, the cost of the electrode is significantly reduced since the amount of these expensive materials is minimized. Reduction of the amount of anode and cathode materials allows the amount of enzyme material used in layer 28 to be increased without significantly changing the cost of the electrode The increased enzyme provides a much larger signal from the electrode with a better response.

Many modifications and variations of the present invention are possible in light of the above teachings. Thus, it is to be understood that, within the scope of the appended claims, the invention may be practiced other than as specifically described.

What is claimed and sought to be secured by Letters Patent of the United States is:

1. A method of fabricating an electrode, comprising the steps of:
   fabricating an opening in a layer of cathodic material;
   fabricating an opening in a layer of dielectric material;
   laminating said layer of cathodic material to one side of said layer of dielectric material and laminating a layer of anodic material to the opposite side of said layer of dielectric material such that the opening in the layer of dielectric material and the opening in the layer of cathodic material are aligned to form a working area;
   inserting glucose oxidase in said working area onto at least a portion of said layer of anodic material; and
   applying a glucose permeable, silicon water-based elastomer over said glucose oxidase in the aligned openings forming said working area.

2. The method of claim 1 in which the layer of cathodic material, the layer of dielectric material and the layer of anodic material are severed to form an individual electrode following lamination of said layers.

3. The method of claim 1 in which the glucose permeable, silicon water-based elastomer is cured after being applied over the glucose oxidase in said working area.

4. The method of claim 1 in which the layer of cathodic material and the layer of anodic material are laminated to the layer of dielectric material simultaneously.

5. The method of claim 1 which further includes connecting separate electrical connectors to said layer of cathodic material and to said layer of anodic material.

* * * * *